(12) United States Patent
Doyle

(10) Patent No.: US 7,594,508 B2
(45) Date of Patent: Sep. 29, 2009

(54) VENTILATION SYSTEM EMPLOYING SYNCHRONIZED DELIVERY OF POSITIVE AND NEGATIVE PRESSURE VENTILATION

(75) Inventor: Peter R. Doyle, Vista, CA (US)

(73) Assignee: RIC Investments, LLC., Wilmington, DE (US)

(*) Notice: Subject to any disclaimer, the term of this patent is extended or adjusted under 35 U.S.C. 154(b) by 0 days.

(21) Appl. No.: 11/771,061

(22) Filed: Jun. 29, 2007

(65) Prior Publication Data
US 2008/0149099 A1    Jun. 26, 2008

Related U.S. Application Data

(60) Provisional application No. 60/830,529, filed on Jul. 13, 2006.

(51) Int. Cl.
*A61M 16/00* (2006.01)
(52) U.S. Cl. .................... 128/204.18; 128/204.21; 128/204.23
(58) Field of Classification Search ............ 128/204.18, 128/204.21, 204.24, 205.24; 601/41, 43, 601/44
See application file for complete search history.

(56) References Cited

U.S. PATENT DOCUMENTS

| | | | |
|---|---|---|---|
| 3,577,977 A | 5/1971 | Ritzinger, Jr. et al. | |
| 4,655,213 A | 4/1987 | Rapoport et al. | |
| 5,188,098 A * | 2/1993 | Hoffman et al. | 128/204.23 |
| 5,222,478 A | 6/1993 | Scarberry et al. | |
| 5,245,995 A | 9/1993 | Sullivan et al. | |
| 5,299,599 A | 4/1994 | Farmer et al. | |
| 5,343,878 A | 9/1994 | Scarberry et al. | |
| 6,209,540 B1 * | 4/2001 | Sugiura et al. | 128/204.18 |
| 6,910,479 B1 * | 6/2005 | Van Brunt | 128/204.18 |
| 7,296,573 B2 * | 11/2007 | Estes et al. | 128/204.23 |

\* cited by examiner

*Primary Examiner*—Steven O Douglas

(57) ABSTRACT

A ventilation system is adapted to synchronize the delivery of both positive pressure ventilation and negative pressure ventilation to a patient. The ventilation system is structured to produce a positive pressure flow of gas which is delivered to the patient's airway and a negative pressure flow of gas which is converted into a negative extrathoracic pressure. The negative extrathoracic pressure is communicated to the patient in synchronism with the delivery of the positive pressure flow of gas.

24 Claims, 5 Drawing Sheets

VENTILATION SYSTEM EMPLOYING SYNCHRONIZED DELIVERY OF POSITIVE AND NEGATIVE PRESSURE VENTILATION

CROSS-REFERENCE TO RELATED APPLICATIONS

This application claims priority under 35 U.S.C. § 119(e) from provisional U.S. patent application No. 60/830,529 filed Jul. 13, 2006 the contents of which are incorporated herein by reference.

BACKGROUND OF THE INVENTION

1. Field of the Invention

The present invention pertains to mechanically assisted ventilatory support and more particularly to a ventilation system which synchronizes the delivery of positive pressure ventilation and negative pressure ventilation to provide improved total ventilatory support to a patient.

2. Description of the Related Art

Mechanically assisted ventilatory support may be delivered to a patient either invasively or non-invasively. Invasive ventilation generally requires endotracheal intubation (i.e., insertion of a breathing tube into the patient's airway) or a tracheostomy (i.e., creation of an artificial opening in the patient's trachea to which a breathing tube is inserted). Non-invasive ventilation (NIV) refers to the delivery of mechanically assisted ventilatory support to a patient without endotracheal intubation or tracheostomy.

NIV was originally delivered to the patient using negative pressure systems having a negative pressure generator and a thoracic interface such as, without limitation, a body tank (also referred to as an "iron lung"), a chest cuirass (also referred to as a "tortoise shell"), and a body wrap (also referred to as a "jacket"). Negative pressure generators are generally designed to provide a negatively pressured source of gas to the thoracic interface. The thoracic interface converts the negatively pressured source of gas into a negative extrathoracic pressure which is communicated to the patient.

Negative pressure generators are generally controlled such that the negative extrathoracic pressure is intermittently applied to the patient. Application of negative extrathoracic pressure causes the patient's chest cavity to expand thereby creating a sub-atmospheric pressure within the patient's lungs. A breathing gas (e.g., air), which is generally at atmospheric pressure, is drawn into the patient's airway and inflates the lungs. Removal of the negative extrathoracic pressure allows the patient's chest cavity to naturally recoil thereby expelling the breathing gas from the lungs.

Negative pressure systems have several limitations. For example, the thoracic interface requires seals around the patient's neck and/or thorax. These seals are difficult to maintain. As a result, it is difficult to efficiently communicate the negative extrathoracic pressure to the patient. Additionally, negative pressure systems are often limited with respect to triggering and cycling of breaths due to the large compliance of the thoracic interface.

More recently, positive pressure systems have replaced negative pressure systems as the preferred manner of providing NIV. Positive pressure systems may have a positive pressure generator and a patient interface. Positive pressure generators include, without limitation, ventilators, pressure support devices (such as a continuous positive airway pressure device, or CPAP device), variable pressure devices (e.g., BiPAP®, Bi-Flex®, or C-Flex™ devices manufactured and distributed by Respironics, Inc. of Pittsburgh, Pa.), and auto-titration pressure support systems. Positive pressure devices are generally designed to provide a positively pressured source of breathing gas to the patient's airway via the patient interface (e.g., a nasal mask, a full-face mask, a total face mask, or a mouthpiece). The positively pressured breathing gas prevents the patient's airway from collapsing (i.e., splints open the patient's airway) so that respiration remains uninterrupted.

Positive pressure systems were developed to overcome many of the problems associated with, negative pressure systems. Positive pressure systems, however, have their own distinct limitations. For example, the effectiveness of a positive pressure system is limited by the ability to maintain a low level of leakage between the patient interface and the patient's face. Additionally, the pressure at which the supply of breathing gas is delivered is limited by a patient's relatively low glottic opening pressure, which if exceeded, may result in gastric distention. Furthermore, positive pressure ventilatory support is lost when the patient removes the patient interface, for example, to talk, eat, or drink.

Accordingly, a need exists for an improved ventilation system which overcomes these and other problems associated with known systems and which provides improved ventilatory support.

SUMMARY OF THE INVENTION

In accordance with an aspect of the present invention, a ventilation system comprises a device structured to deliver positive pressure ventilation and negative pressure ventilation to a patient, and a controller structured to synchronize delivery of the positive pressure ventilation and the negative pressure ventilation to the patient.

According to another aspect of the present invention, a ventilation system comprises a device structured to deliver a positive pressure flow of gas and a negative extrathoracic pressure to a patient, and a controller structured to synchronize delivery of the positive pressure flow of gas and the negative extrathoracic pressure to the patient.

According to another aspect of the present invention, a method for ventilating a patient which comprises generating a positive pressure flow of gas, generating a negative extrathoracic pressure, and synchronizing the delivery of the positive pressure flow of gas and the negative extrathoracic pressure to the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
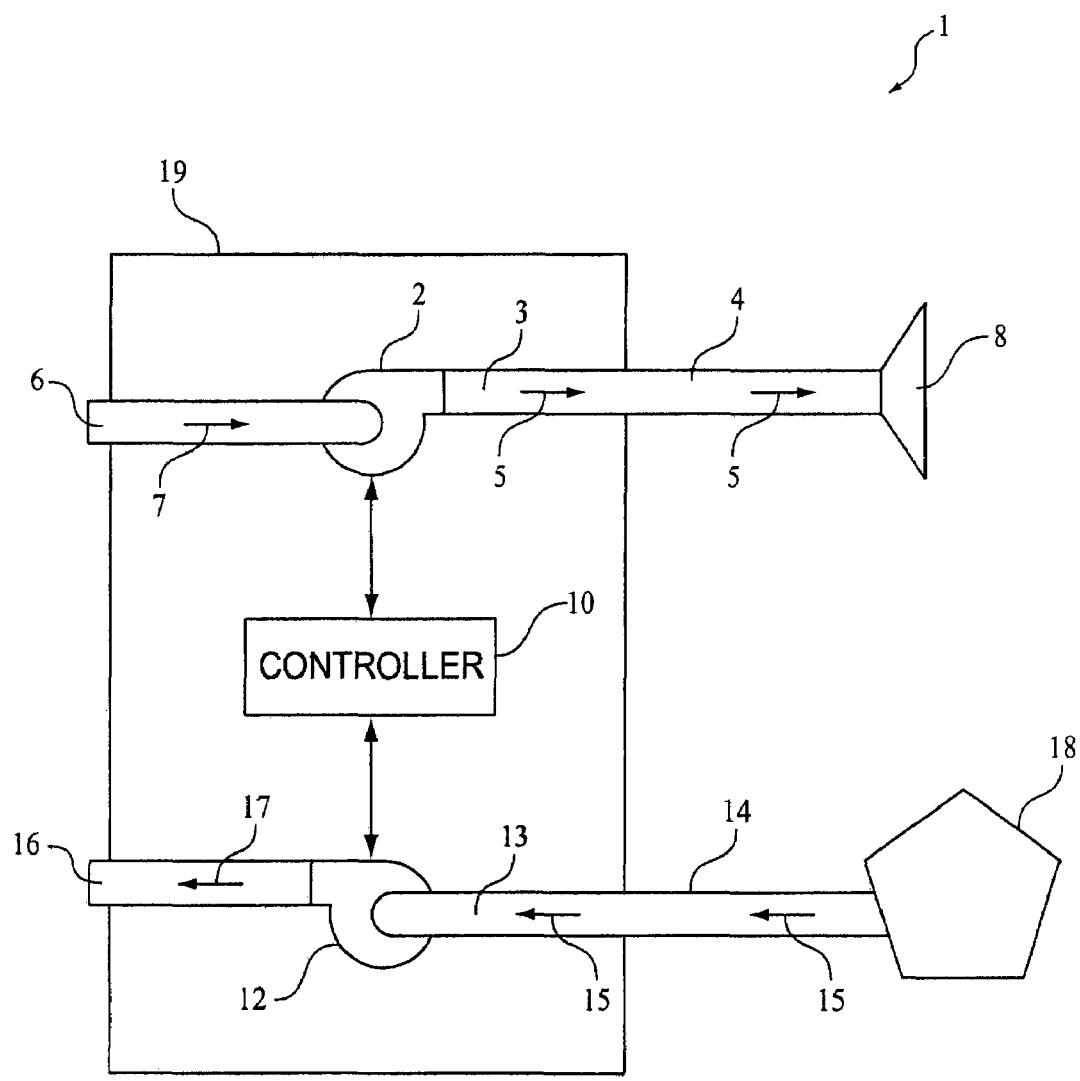
FIG. 1 is a schematic view of a ventilation system according to one embodiment.

Directional phrases used herein, such as, for example, left, right, clockwise, counterclockwise, top, bottom, up, down, and derivatives thereof, relate to the orientation of the elements shown in the drawings and are not limiting upon the claims unless expressly recited therein.

As employed herein, the term "number" shall mean one or more than one and the singular form of "a", "an", and "the" include plural referents unless the context clearly indicates otherwise.

As employed herein, the statement that two or more parts are "connected" or "coupled" together shall mean that the parts are joined together either directly or joined together through one or more intermediate parts. Further, as employed herein, the statement that two or more parts are "attached" shall mean that the parts are joined together directly.

The present invention is directed to a ventilation system which is adapted to synchronize the delivery of both positive pressure ventilation and negative pressure ventilation to a patient. The ventilation system, for example, may be structured to produce a positive pressure flow of gas and a negative flow of gas. The positive pressure flow of gas is delivered to the patient's airway and the negative pressure flow of gas is converted into a negative extrathoracic pressure. The negative extrathoracic pressure is communicated to the patient in synchronism with the delivery of the positive pressure flow of gas. For example, both the positive pressure flow of gas and the negative extrathoracic pressure are delivered to the patient during the inhalation phase; whereas the positive pressure flow of gas and the negative extrathoracic pressure are not delivered, or a reduced amount of positive pressure flow of gas and/or the negative extrathoracic pressure is delivered, during the exhalation phase.

By synchronizing the delivery of the positive pressure flow of gas and the negative extrathoracic pressure, increased ventilation efficiency is achieved. More specifically, by employing a combination of positive pressure and negative pressure, a higher trans-thoracic pressure is provided without the onset of gastric insufflation. Stated in another way, the total amount of trans-thoracic pressure which is delivered to the patient through a combination of positive pressure and negative pressure (i.e., a "delta pressure") is greater than the pressure which can be delivered to the patient by either positive pressure or negative pressure alone.

For example, application of positive pressure alone is limited to approximately 30 cm $H_2O$ because of the relatively low glottic opening pressure (which may lead to gastric insufflation). Application of negative pressure alone is limited to approximately −30 cm $H_2O$ due to sealing limitations of the thoracic interface and due to possible closure of the patient's upper airway. However, delta pressures of greater than 30 cm $H_2O$ (e.g., approximately 20 cm $H_2O$ of positive pressure and approximately −20 cm $H_2O$ of negative pressure) can be applied in synchrony without experiencing these adverse effects. Additionally, because the negative pressure system is employed to augment inspiration, the positive pressure system can be prescribed to provide a lower inspiratory positive airway pressure (IPAP). For example, the positive pressure can be reduced from 25 cm $H_2O$ to 20 cm $H_2O$. As a result, patient comfort and compliance increase.

Additionally, the combination of positive pressure and negative pressure allows the patient to remove the positive pressure interface (e.g., mask) to eat or communicate without losing the ventilatory support supplied by the negative pressure system. Likewise, the negative pressure interface (e.g., chest cuirass) can be opened/removed (for example, to allow access to a health care provider) without the patient loosing the ventilatory support supplied by the positive pressure system.

A ventilation system 1 according to one embodiment of the present invention is shown in FIG. 1. Ventilation system 1 includes a housing 19 containing a positive gas flow generator 2, a negative gas flow generator 12, and a controller 10. Positive gas flow generator 2 includes an inlet conduit 6 and a discharge conduit 3, each of which extends through housing 19. As used herein, the term "conduit" corresponds to any structure suitable for communicating a flow of gas; a typical conduit is a flexible tube. Inlet gas (represented by arrow 7) is supplied to positive gas flow generator 2 by inlet conduit 6. Positive gas flow generator 2 discharges a positive pressure flow of gas (represented by arrow 5) through discharge conduit 3. The positive pressure flow of gas 5 is delivered to the airway of a patient (not shown) via a first conduit 4 and a patient interface 8 which are coupled with discharge conduit 3. In the current embodiment, positive pressure generator 2 supplies positive pressure flow of gas 5 at a range between approximately 4 cm $H_2O$ and approximately 30 cm $H_2O$, although it is contemplated that this pressure range may be varied while remaining within the scope of the present invention.

A negative pressure flow of gas 15 is produced by negative gas flow generator 12. Negative gas flow generator 12 includes an inlet conduit 13 and a discharge conduit 16, each of which extends through housing 19. In the current embodiment, a patient (not shown) is fitted with a thoracic interface 18. Thoracic interface 18 is operatively coupled to inlet conduit 13 via a second conduit 14. Negative pressure generator 12 removes air from thoracic interface 18. Specifically, in the current embodiment, negative pressure generator 12 creates negative pressure flow of gas (represented by arrow 15) at a pressure range between approximately −5 cm $H_2O$ and approximately −100 cm $H_2O$. Negative gas flow generator 12 discharges an outlet gas (represented by arrow 17) to atmosphere via a discharge conduit 16. It is contemplated that the pressure range of the negative pressure flow of gas may be varied while remaining within the scope of the present invention.

Positive gas flow generator 2, first conduit 4, and patient interface 8 may be referred to as the "positive pressure component". Likewise, negative gas flow generator 12, second conduit 14, and thoracic interface 18 may be referred to as the "negative pressure component".

Controller 10 is operatively connected to both positive pressure generator 2 and negative pressure generator 12. Controller 10 may receive feedback from, and be responsive to, a number of sensors (not shown) such as, without limitation, flow transducers, temperature transducers, pressure transducers, vibrations transducers, and sound transducers. Controller 10 is adapted to synchronize the delivery of positive pressure flow of gas 5 to patient interface 8 and negative pressure flow of gas 15 to thoracic interface 18. Ventilation system 1, for example, is adapted to provide a specific inspiratory positive airway pressure (IPAP) to the patient in the current embodiment. Specifically, controller 10 is adapted such that ventilation system 1 delivers a first portion of the IPAP though the application of positive pressure flow of gas 5 and a second portion of the IPAP through the application of negative extrathoracic pressure (which is dependent upon the negative pressure flow of gas 15).

Although described above in conjunction with IPAP, it is contemplated that controller 10 can be adapted to synchronize the delivery of the positive pressure flow of gas 5 and the negative extrathoracic pressure responsive to another parameter or combination of parameters such as, without limitation, positive end expiratory pressure (PEEP), the patient's respiratory rate, a ventilatory cycle triggering event, detection of a leak related to the positive pressure flow of gas, detection the a loss of negative extrathoracic pressure, detection of non-delivery of the positive pressure flow of gas 5 to the patient, and detection of non-delivery of the negative extrathoracic pressure to the patient.

For example, controller 10 may synchronize the negative pressure generator 12 to provide an equivalent of PEEP and the positive pressure generator 2 to provide no PEEP while still providing IPAP. As another example, controller 10 may synchronize delivery of the positive pressure flow of gas 5 and the negative extrathoracic pressure in response to patient's respiratory rate during normal use. However when the patient removes the patient interface (e.g., to eat), controller 10 may synchronize delivery of the positive pressure flow of gas and the negative extrathoracic pressure in response to detection of non-delivery of the positive pressure flow of gas 5 to the patient (i.e., controller 10 may decrease positive pressure flow of gas 5 and increase the negative extrathoracic pressure).

Figure 2:
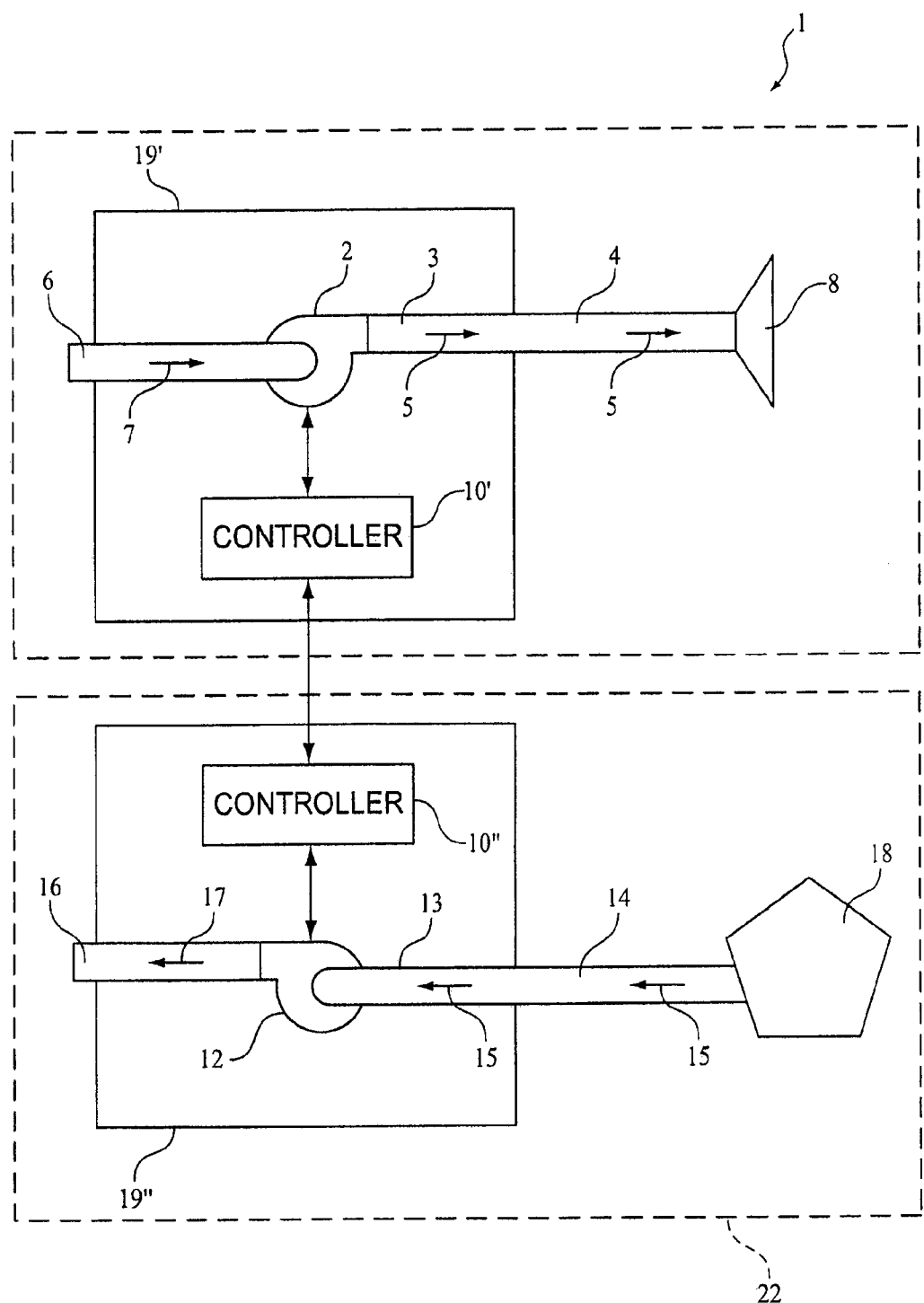
FIG. 2 is a schematic view of a ventilation system according to another embodiment.

It is also contemplated that the actual arrangement of the component parts of ventilation system 1 may be varied while remaining within the scope of the present invention. For example, a ventilation system 1', in which positive pressure component 20 and negative pressure component 22 are separated is shown in FIG. 2. More specifically, positive pressure component 20 (which as discussed above, includes positive gas flow generator 2, first conduit 4, and patient interface 8) is separated from negative pressure component 22 (which, as discussed above, includes negative gas flow generator 12, second conduit 14, and thoracic interface 18).

In the current embodiment, ventilation system 1' is implemented using a number of off-the-shelf items having minor modifications. For example, the positive pressure generator 2 and/or negative pressure generator 12 may include a ventilator, a pressure support device (e.g., a CPAP device), a variable pressure device (e.g., a BiPAP®, Bi-Flex®, or C-Flex™ device manufactured and distributed by Respironics, Inc. of Pittsburgh, Pa.), or an auto-titration pressure support system. BiPAP®, Bi-Flex®, and C-Flex™ devices are pressure support devices in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea, hypopnea, flow limited breathing, upper airway resistance, or snoring.

In the current embodiment, positive pressure component 20 is implemented using a BiPAP® Vision® ventilatory support system and a ComfortLite2™ nasal mask, both from Respironics, Inc. of Murrysville, Pa. Negative pressure component 22 is implemented using an NEV-100 non-invasive extrathoracic ventilator and a Nu-Mo® body suit, both also from Respironics, Inc.

In the current embodiment, the BiPAP® Visions ventilatory support system and the NEV-100 are operated in master/slave configuration. Typically, controller 10' of the BiPAP® Vision® ventilatory support system is adapted to cause the BiPAP® Vision® ventilatory support system to deliver a specific pressure of IPAP (to keep the airway open as a patient breathes in) and relatively lower pressure of expiratory phase air pressure (EPAP) (to reduce the work done by the patient while exhaling). Controller 10' uses feedback signals (e.g., flow rate, pressure, etc.) to determine which phase (i.e., inspiratory or expiratory) of the respiratory cycle the patient is currently experiencing. These same feedback signals may be used to control the operation of the NEV-100 and Nu-Mo® body suit. Specifically, controller 10' of the BiPAP® Vision® ventilatory support system is adapted to communicate with controller 10" of the NEV-100 non-invasive extrathoracic ventilator such that the negative extrathoracic pressure delivered by the NEV-100 non-invasive extrathoracic ventilator and Nu-Mo® body suit is synchronized with the positive pressure flow of gas 5 delivered by the BiPAP® Vision® ventilatory support system and the ComfortLite2™ nasal mask.

Additionally, controller 10" of the NEV-100 non-invasive extrathoracic ventilator is adapted to resume master control over the NEV-100 non-invasive extrathoracic ventilator when needed. For example, upon detecting that the patient has removed the ComfortLite2™ nasal mask (e.g., to eat; communicate), controller 10' of the BiPAP® Vision® ventilatory support system sends a signal to controller 10" of the NEV-100 non-invasive extrathoracic ventilator. Controller 10" then exerts master control over the NEV-100 non-invasive extrathoracic ventilator until reset (e.g., until receiving a signal indicating that the ComfortLite2™ nasal mask has been re-fitted).

It should be apparent to one skilled in the art that FIG. 1 and FIG. 2 are simplified schematics. It should further be apparent that ventilation system 1 and/or ventilation system 1' may include additional components and/or features which have been omitted for clarity, but which may form a part of the present invention. For example, positive pressure generator 2 may have a number of control valves associated therewith. The control valves may be structured to pressure and/or volume of the positive pressure flow of gas 15. Additionally or alternatively, the pressure and/or volume of the positive pressure flow of gas 15 may be controlled by adapting controller 10 and/or controller 10' to regulate the output of positive pressure generator 2.

Figure 3:
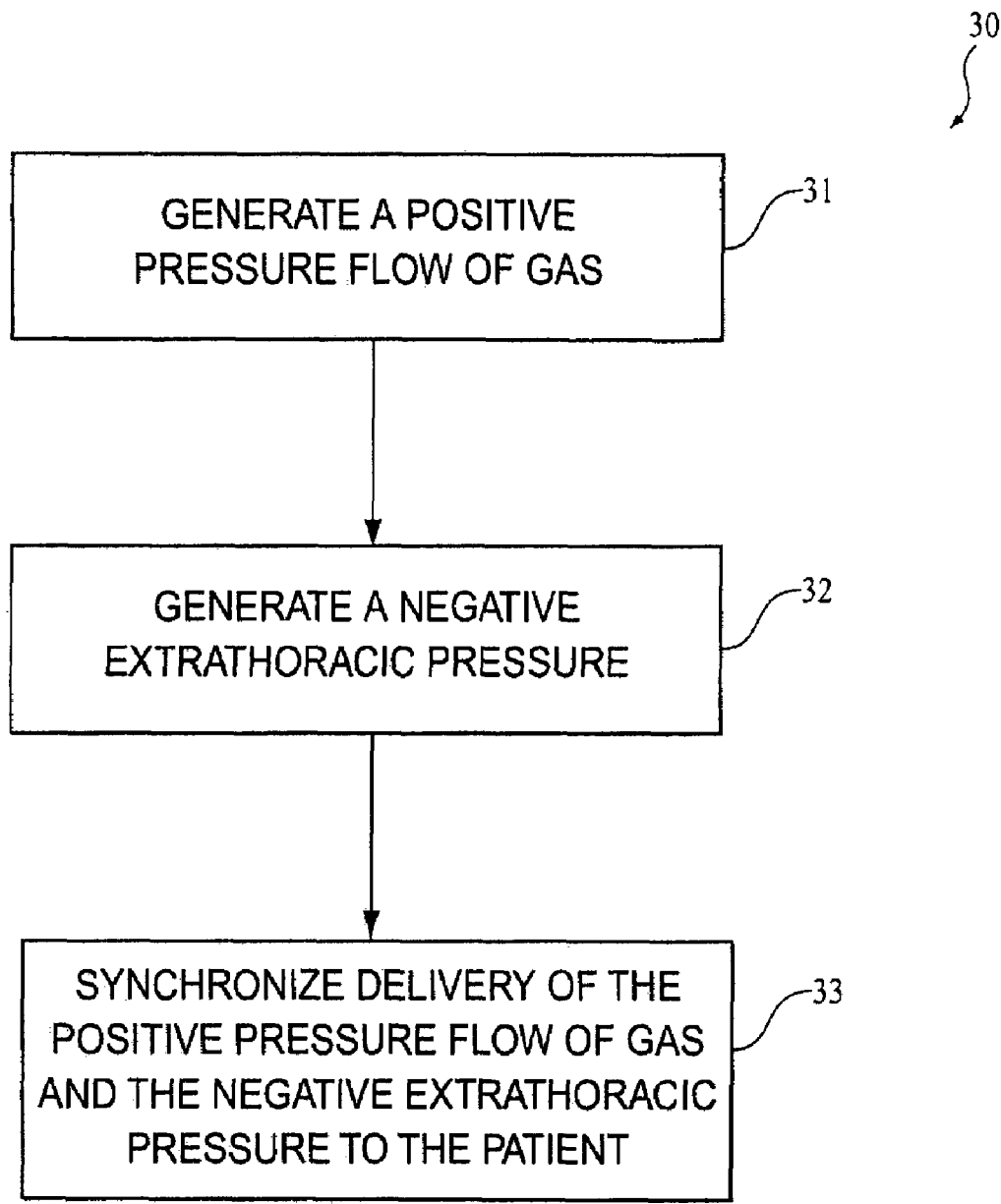
FIG. 3 illustrates an operational process for ventilating a patient according to one embodiment.

FIG. 3 illustrates operational process 30 for ventilating a patient according to an embodiment of the present invention. The discussion of operational process 30 will be directed to its implementation using ventilation system 1, however, it should be apparent that other ventilation systems such as, and without limitation, ventilation system 1' may be employed while remaining within the scope of the present invention.

Operational process 30 is initiated when a positive pressure flow of gas is generated in operation 31. In the current embodiment, controller 10 causes positive pressure generator 2 to generate positive pressure flow of gas 5.

Operational control then passes to operation 32 where a negative extrathoracic pressure is generated. In the current embodiment, controller 10 causes negative pressure generator 12 to generate negative pressure flow of gas 15 which is delivered to thoracic interface 18. Thoracic interface 18 converts negative pressure flow of gas 15 into a negative extrathoracic pressure.

Operational control then passes to operation 33 delivery of the positive pressure flow of gas is synchronized with the delivery of the extrathoracic pressure. In the current embodiment, controller 10 is adapted to synchronize positive pressure generator 2 and negative pressure generator 12 such that a first portion of the IPAP is delivered though the application of positive pressure flow of gas 5 and a second portion of the IPAP is delivered through the application of negative extrathoracic pressure. For example, controller 10 uses feedback signals (e.g., flow rate, pressure, etc.) from positive pressure generator 2 to determine which phase (i.e., inspiratory or expiratory) of the respiratory cycle the patient is currently experiencing and to determine what portion of the IPAP the patient is receiving from the positive pressure flow of gas 5. These feedback signals are the used to control the operation of negative pressure generator 12 such that the correct amount of negative extrathoracic pressure (i.e., the amount necessary to provide the second portion of the IPAP) is applied to the patient during the inspiratory phase and is removed or reduce during the expiratory phase. As discussed above in conjunction with FIG. 1, controller 10 may employ parameters other than IPAP to synchronize delivery of the positive pressure flow of gas and the negative extrathoracic pressure.

Figure 4:
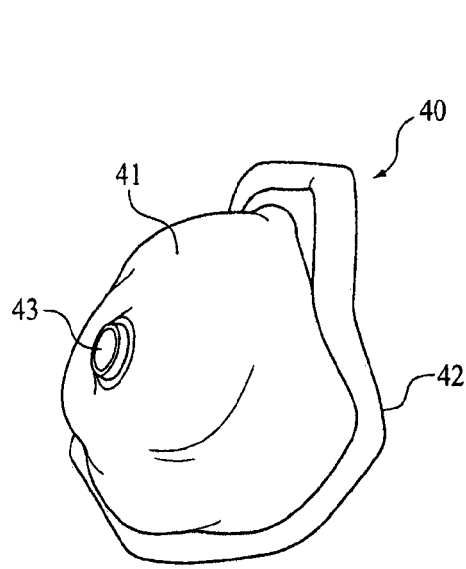
FIG. 4 is a perspective view of a chest cuirass for use with the ventilation systems of FIGS. 1-2.
Figure 5:
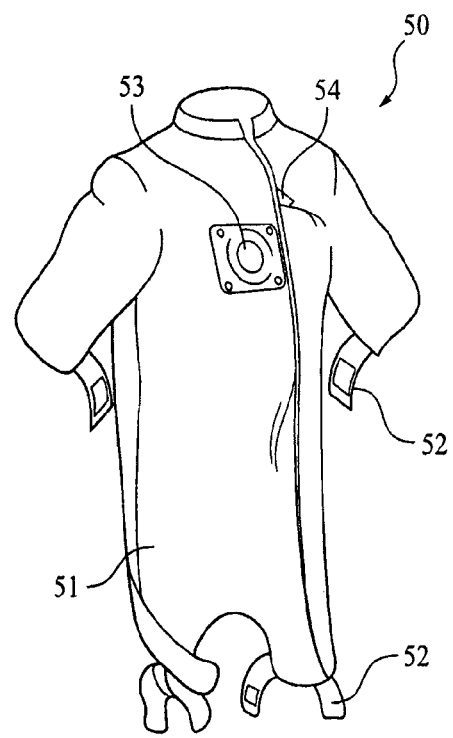
FIG. 5 is a perspective view of a chest wrap for use with the ventilation systems of FIGS. 1-2.
Figure 6:
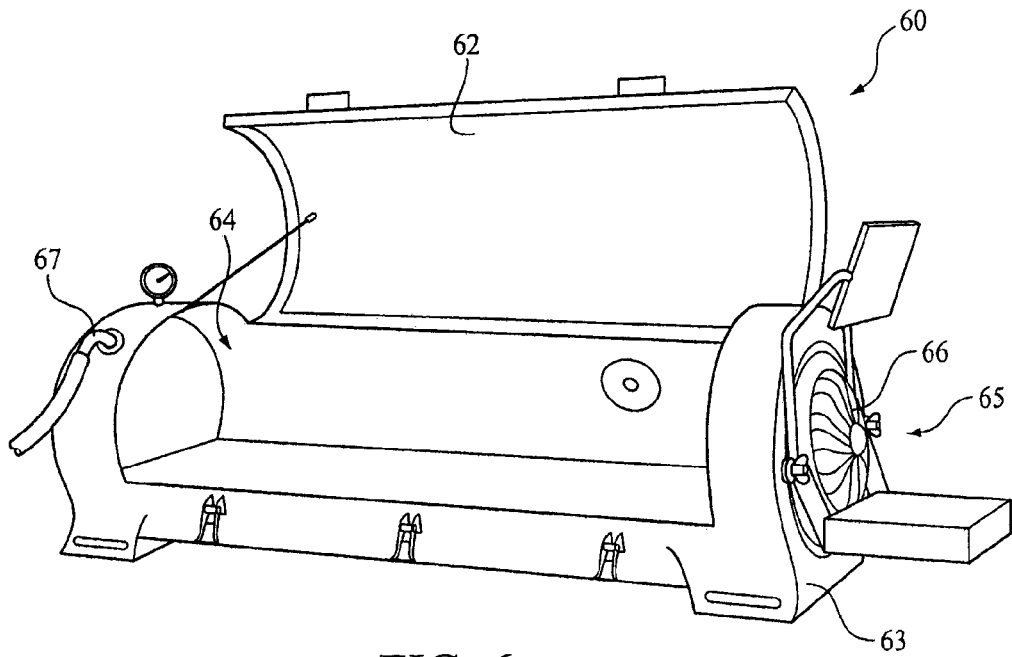
FIG. 6 is a perspective view of a body tank for use with the ventilation systems of FIGS. 1-2.

FIGS. 4-6 illustrate various exemplary thoracic interfaces 18 that may be employed with ventilation system 1 and ventilation system 1'. It is contemplated, however, that other thoracic interfaces 18 may be used while remaining within the scope of the present invention. For example, an electro-mechanical operator structured to generate the extrathoracic pressure and to deliver the negative extrathoracic pressure to a patient may be used.

Referring now to FIG. 4, a chest cuirass 40 (such as, without limitation, the Soft Shell Chest Shell cuirass from Respironics, Inc. of Murrysville, Pa.) for use with ventilation system 1 and ventilation system 1' is shown. Chest cuirass 40 includes a hard shell 41 with a sealing cushion 42 disposed around the edge thereof. Chest cuirass 40 is placed over the patient's chest and abdomen and secured to the patient with a number of straps (not shown). Shell 41 and sealing cushion 42 provide a small chamber over the patient's chest and abdomen. An orifice 43 is structured to couple with negative pressure generator 12 (such as, without limitation, the NEV-100 non-invasive extrathoracic ventilator also from Respironics, Inc.). Orifice 43 extends through shell 41 such that inlet conduit 13 of negative pressure generator 12 is in fluid communication with the small chamber over the patient's chest and abdomen. Chest cuirass 40 is structured to convert negative pressure flow of gas 15 from negative pressure generator 12 into a negative extrathoracic pressure which is delivered to the patient.

FIG. 5 illustrates a body wrap 50 (such as, without limitation, the Nu-Mo® body suit from Respironics, Inc.) for use with ventilation system 1 and ventilation system 1'. When worn, body wrap 50 is structured to cover the patient's chest and abdomen. Body wrap 50 includes a fabric 51 which is impervious to air. Body wrap 50 is sealed using a zipper 54 and number of straps 52. An orifice 53 is structured to couple with negative pressure generator 12 (such as, without limitation, the NEV-100 non-invasive extrathoracic ventilator). Orifice 53 extends through fabric 51 such that negative inlet conduit 13 of pressure generator 12 is in fluid communication with the space between body wrap 50 and the patient's body. Body wrap 50 is structured to convert negative pressure flow of gas 15 from negative pressure generator 12 into a negative extrathoracic pressure which is delivered to the patient.

FIG. 6 illustrates a body tank 60 (such as, without limitation, the Porta-Lung® body tank manufactured by Porta-Lung, Incorporated of Denver, Colo.) for use with ventilation system 1 and ventilation system 1'. Tank 60 includes a cylindrical base 63 with a door 62. One end of tank 60 includes an opening 65 having a sealing skirt 66. A patient climbs inside of chamber 64 and places his/her head through opening 65 such that shirt 66 creates a seal around the patient's neck. Door 62 is then closed and secured to base 63, thus forming an air tight chamber 64. Tank 60 covers the patient's whole body, excluding their head. An orifice 67 extends through base 63 and is coupled to inlet conduit 13 such that negative pressure generator 12 is in fluid communication with the chamber 64. Accordingly, tank 60 is structured to convert negative pressure flow of gas 15 from negative pressure generator 12 into a negative extrathoracic pressure which is delivered to the patient.

Figure 7:
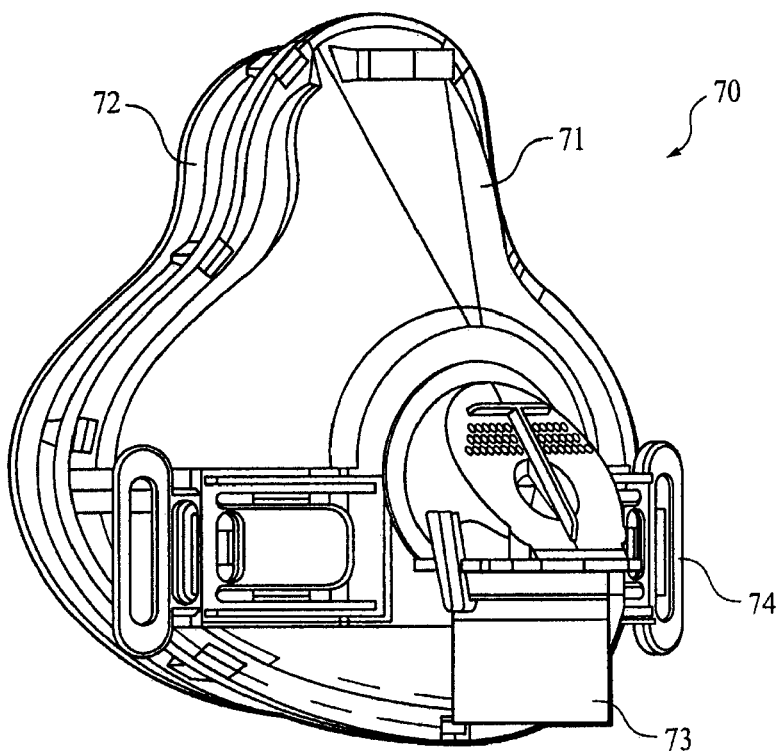
FIG. 7 is a perspective view of a full-face mask for use with the ventilation systems of FIGS. 1-2.
Figure 8:
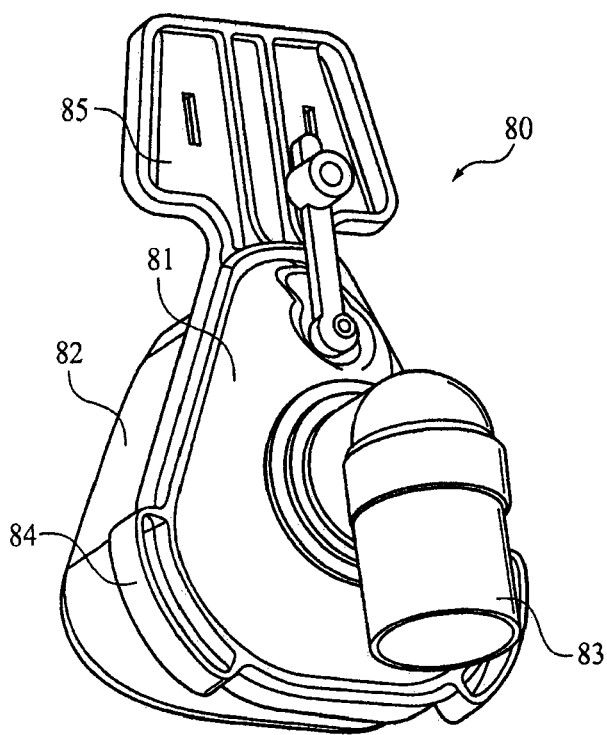
FIG. 8 is a perspective view of a nasal mask for use with the ventilation systems of FIGS. 1-2.

FIGS. 7-8 illustrate various exemplary patient interfaces 8 that may be employed with ventilation system 1 and ventilation system 1'. It is contemplated, however, that other patient interfaces 8 may be used while remaining within the scope of the present invention.

Referring now to FIG. 7, a full-face mask 70 (such as, without limitation, a ComfortFull™ Full-Face Mask from Respironics, Inc. of Murrysville, Pa.) for use with ventilation system 1 and ventilation system 1' is shown. Mask 70 includes a polycarbonate shell 71 with a cushion 72 disposed around the edge thereof. Mask 70 is adapted to be placed over the patient's nose and mouth and secured to the patient with a headgear having a number of straps (not shown) which are looped through associated connectors 74. Shell 71 and cushion 72 provide a small chamber over the patient's nose and mouth. An elbow 73 is structured to couple with positive pressure generator 2 (such as, without limitation, the BiPAP® Vision® ventilatory support system from Respironics, Inc.). Elbow 73 also couples with an orifice (not shown) that extends through shell 71 such that, when connected, positive pressure generator 2 is in fluid communication with the small chamber over the patient's nose and mouth. Mask 70 is structured to deliver positive pressure flow of gas 5 from positive pressure generator 2 to the patient's airway.

FIG. 5 illustrates a nasal mask 80 (such as, without limitation, a ComfortClassic™ Nasal Mask from Respironics, Inc. of Murrysville, Pa.) for use with ventilation system 1 and ventilation system 1'. Mask 80 includes a polycarbonate shell 81 with a cushion 82 disposed around the edge thereof. Mask 80 is adapted to be placed over the patient's nose and secured to the patient with a headgear having a number of straps (not shown) which are looped through associated connectors 84 and connected to a forehead support 85. Shell 81 and cushion 82 provide a small chamber over the patient's nose. An elbow 83 is structured to couple with positive pressure generator 2 (such as, without limitation, the BiPAP® Vision® ventilatory support system from Respironics, Inc.). Elbow 83 also couples with an orifice (not shown) that extends through shell 81 such that, when connected, positive pressure generator 2 is in fluid communication with the small chamber over the patient's nose. Mask 80 is structured to deliver positive pressure flow of gas 5 from positive pressure generator 2 to the patient's airway.

Although the present invention has been described in the context of non-invasive delivery of the positive pressure ventilation and the negative pressure ventilation, it is contemplated that the positive pressure ventilation and/or the negative pressure ventilation may be delivered to the patient invasively (e.g., via an endotracheal tube, a tracheostomy tube, a laryngeal mask airway, etc.). For example, positive pressure component 20 may include a ventilator (such as, without limitation, a PLV® Continuum™ portable ventilator from Respironics, Inc.) and an endotracheal tube (such as, without limitation, an endotracheal tube from Mallinckrodt, Shiley, Portex, or Bivona) for invasive delivery of the positive pressure ventilation.

Furthermore, although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A ventilation system, comprising:
    a device structured to deliver positive pressure ventilation and negative pressure ventilation to a patient; and
    a controller structured to cause the device to deliver a desired total pressure ventilation to the patient by synchronizing delivery of both a particular positive pressure ventilation and a particular negative pressure ventilation to the patient during an inhalation phase.

2. The ventilation system of claim 1, wherein the device comprises:
    a positive pressure component; and
    a negative pressure component.

3. The ventilation system of claim 2, wherein:
    the positive pressure component, comprises:
        a positive gas flow generator structured to generate a positive pressure flow of gas comprising the particular positive pressure ventilation;
        a first conduit; and
        a patient interface, wherein the first conduit and the patient interface are structured to communicate the positive pressure flow of gas from the positive gas flow generator to an airway of the patient, and wherein
    the negative pressure component, comprises:
        a negative gas flow generator structured to generate a negative pressure flow of gas;
        a second conduit; and
        a thoracic interface, wherein the second conduit is structured to communicate the negative pressure flow of gas from the negative gas flow generator to the thoracic interface, and wherein the thoracic interface is structured to convert the negative pressure flow of gas into a negative extrathoracic pressure and to communicate the negative extrathoracic pressure to the patient, the negative extrathoracic pressure comprising the particular negative pressure ventilation.

4. The ventilation system of claim 3, wherein the controller is adapted to synchronize the delivery of the positive pressure flow of gas and the negative extrathoracic pressure to the patient during the inhalation phase in response to at least one of such a patient's respiratory rate, a positive end expiratory pressure, a ventilatory cycle triggering event, detection of leakage of an amount of the positive pressure flow of gas, detection of loss of an amount of negative extrathoracic pressure, non-delivery of the positive pressure flow of gas to the patient, and non-delivery of the negative extrathoracic pressure to the patient.

5. The ventilation system of claim 3, wherein the positive gas flow generator is contained within a first housing, and wherein the negative gas flow generator is contained within a second housing.

6. A ventilation system, comprising:
    a device structured to deliver a positive pressure flow of gas and a negative extrathoracic pressure to a patient; and
    a controller structured to cause the device to deliver a desired total pressure ventilation to the patient by synchronizing delivery of both the positive pressure flow of gas and the negative extrathoracic pressure to the patient during an inhalation phase.

7. The ventilation system of claim 6, wherein the device comprises:
    a gas flow generator structured to generate at least one of the positive pressure flow of gas and a negative pressure flow of gas.

8. The ventilation system of claim 7, wherein the device further comprises:
    a patient conduit structured to couple with the gas flow generator; and
    a patient interface structured to couple with the patient conduit, wherein the patient conduit and the patient interface are structured to communicate the positive pressure flow of gas from the gas flow generator to an airway of the patient.

9. The ventilation system of claim 8, wherein the patient interface includes at least one of a nasal mask, a full-face mask, a total face mask, an endotracheal tube, a tracheostomy tube, and a laryngeal mask airway.

10. The ventilation system of claim 8, wherein the patient interface is structured to invasively deliver the positive pressure flow of gas to the airway of the patient.

11. The ventilation system of claim 8, wherein the patient interface is structured to non-invasively deliver the positive pressure flow of gas to the airway of the patient.

12. The ventilation system of claim 7, wherein the device further comprises:
    a patient conduit structured to couple with the gas flow generator; and
    a thoracic interface structured to couple with the patient conduit, wherein the patient conduit is structured to communicate the negative pressure flow of gas from the gas flow generator to the thoracic interface, and wherein the thoracic interface is structured to convert the negative pressure flow of gas into the negative extrathoracic pressure and to communicate the negative extrathoracic pressure to the patient.

13. The ventilation system of claim 12, wherein the thoracic interface includes at least one of a body tank system, a chest cuirass, and a body wrap.

14. The ventilation system of claim 6, wherein the device comprises:
    an electro-mechanical operator structured to generate the extrathoracic pressure and to deliver the negative extrathoracic pressure to the patient.

15. The ventilation system of claim 6, wherein the controller is adapted to cause the device to deliver to the patient a first portion of an inspiratory positive airway pressure by application of the positive pressure flow of gas and a second portion of the inspiratory positive airway pressure by application of the negative extrathoracic pressure.

16. The ventilation system of claim 6, wherein the controller is adapted to synchronize the delivery of both the positive pressure flow of gas and the negative extrathoracic pressure during the inhalation phase in response to at least one of the patient's respiratory rate, a positive end expiratory pressure, a ventilatory cycle triggering event, detection of leakage of an amount of the positive pressure flow of gas, detection of loss of an amount of negative extrathoracic pressure, non-delivery of the positive pressure flow of gas to the patient, and non-delivery of the negative extrathoracic pressure to the patient.

17. A method for ventilating a patient, comprising:
generating a positive pressure flow of gas;
generating a negative extrathoracic pressure; and
delivering a desired total pressure ventilation to the patient by synchronizing delivery of both the positive pressure flow of gas and the negative extrathoracic pressure to the patient during an inhalation phase.

18. The method of claim 17, wherein generating a positive pressure flow of gas comprises producing the positive pressure flow of gas with at least one of a ventilator, a Bi-PAP device, a CPAP device, and pressurized bottle of gas.

19. The method of claim 17, wherein generating a negative extrathoracic pressure comprises:
generating a negative pressure flow of gas; and
communicating the negative pressure flow of gas to a thoracic interface.

20. The method of claim 17, wherein synchronizing the delivery of both the positive pressure flow of gas and the negative extrathoracic pressure to the patient during the inhalation phase comprises communicating the positive pressure flow of gas non-invasively to the patient.

21. The method of claim 17, wherein synchronizing the delivery of both the positive pressure flow of gas and the negative extrathoracic pressure to the patient during the inhalation phase comprises communicating the positive pressure flow of gas invasively to the patient.

22. The method of claim 17, wherein synchronizing the simultaneous delivery of both the positive pressure flow of gas and the negative extrathoracic pressure to the patient during the inhalation phase comprises:
selecting an inspiratory positive airway pressure;
communicating the positive pressure flow of gas to the patient to provide a first percentage of the inspiratory positive airway pressure during an inspiratory phase; and
communicating the negative extrathoracic pressure to the patient to provide a second percentage of the inspiratory positive airway pressure during the inspiratory phase.

23. The method of claim 17, wherein synchronizing the delivery of both the positive pressure flow of gas and the negative extrathoracic pressure to the patient during the inhalation phase comprises:
determining a delta pressure, wherein the absolute value of the delta pressure is greater than the amount of positive pressure which causes the onset of gastric insufflation; and
communicating the positive pressure flow of gas and the negative extrathoracic pressure to the patient to provide the delta pressure, wherein the amount of the positive pressure flow of gas communicated is less than the amount of positive pressure which causes the onset of gastric insufflation.

24. The method of claim 17 wherein synchronizing the delivery of both the positive pressure flow of gas and the negative extrathoracic pressure to the patient during the inhalation phase comprises:
delivering the positive pressure flow of gas and the negative extrathoracic pressure to the patient in response to at least one of such a patient's respiratory rate, a positive end expiratory pressure, a ventilatory cycle triggering event, detection of leakage of an amount of the positive pressure flow of gas, detection of loss of an amount of negative extrathoracic pressure, non-delivery of the positive pressure flow of gas to the patient, and non-delivery of the negative extrathoracic pressure to the patient.

\* \* \* \* \*